(12) United States Patent
Scott-Young (10) Patent No.: US 10,952,870 B2
(45) Date of Patent: Mar. 23, 2021

(54) SPINAL FIXATION AND GUIDANCE SYSTEM AND METHOD

(71) Applicant: Prism Surgical Designs Pty Ltd., Red Hill (AU)

(72) Inventor: Matthew Scott-Young, Red Hill (AU)

(73) Assignee: PRISM SURGICAL DESIGNS PTY LTD., Red Hill (AU)

( * ) Notice: Subject to any disclaimer, the term of this patent is extended or adjusted under 35 U.S.C. 154(b) by 187 days.

(21) Appl. No.: 16/320,977

(22) PCT Filed: Jul. 26, 2017

(86) PCT No.: PCT/AU2017/050774
§ 371 (c)(1),
(2) Date: Jan. 25, 2019

(87) PCT Pub. No.: WO2018/018084
PCT Pub. Date: Feb. 1, 2018

(65) Prior Publication Data
US 2019/0167442 A1     Jun. 6, 2019

(30) Foreign Application Priority Data

Jul. 26, 2016   (AU) .................................. 2016902926
Jan. 3, 2017    (AU) .................................. 2017100001

(51) Int. Cl.
*A61B 17/70* (2006.01)
*A61B 17/80* (2006.01)
(Continued)

(52) U.S. Cl.
CPC ............ *A61F 2/46* (2013.01); *A61B 17/7059* (2013.01); *A61B 17/7074* (2013.01);
(Continued)

(58) Field of Classification Search
CPC .. A61F 2/46; A61F 2/44; A61F 2/4455; A61F 2/4465; A61F 2/4611;
(Continued)

(56) References Cited

U.S. PATENT DOCUMENTS 9,603,718 B2 *   3/2017  Cheng ..................... A61F 2/447
10,123,829 B1 *  11/2018 Brotman ............ A61B 17/7079
(Continued)

FOREIGN PATENT DOCUMENTS

WO   WO 2010/107692 A1   9/2010
WO   WO 2014/188280 A2   11/2014
WO   WO 2016/205870 A1   12/2016

*Primary Examiner* — Eduardo C Robert
*Assistant Examiner* — David C Comstock
(74) *Attorney, Agent, or Firm* — Knobbe, Martens, Olson & Bear, LLP (57) ABSTRACT

A spinal fixation and guidance system comprising: a spinal cage configured to be received between adjacent first and second vertebrae; and an alignment assembly comprising: a guidance element for guiding one or more fasteners for fastening said spinal cage relative to said adjacent vertebrae; or fastening said spinal plate to adjacent vertebrae and a mating element comprising engagement portions for mating with said guidance elements relative to the spinal cage.

17 Claims, 7 Drawing Sheets

(51) Int. Cl.
*A61B 17/88* (2006.01)
*A61F 2/46* (2006.01)
*A61F 2/44* (2006.01)
*A61F 2/30* (2006.01)

(52) U.S. Cl.
CPC .............. *A61B 17/808* (2013.01); *A61F 2/44* (2013.01); *A61F 2/4455* (2013.01); *A61F 2/4465* (2013.01); *A61F 2/4611* (2013.01); *A61F 2002/30578* (2013.01); *A61F 2002/30787* (2013.01); *A61F 2002/30904* (2013.01)

(58) Field of Classification Search
CPC .. A61F 2002/30578; A61F 2002/30787; A61F 2002/30904; A61B 17/7059; A61B 17/7074; A61B 17/808
USPC ......... 606/246, 248, 279, 280, 281, 286, 99, 606/104, 86 A, 86 B; 623/17.11
See application file for complete search history.

(56) References Cited

U.S. PATENT DOCUMENTS

| | | | |
|---|---|---|---|
| 2008/0033440 A1* | 2/2008 | Moskowitz | A61F 2/4465 606/251 |
| 2011/0098747 A1 | 4/2011 | Donner et al. | |
| 2011/0190892 A1* | 8/2011 | Kirschman | A61F 2/447 623/17.16 |
| 2012/0197401 A1 | 8/2012 | Duncan et al. | |
| 2014/0316419 A1 | 10/2014 | Perry | |
| 2015/0005879 A1 | 1/2015 | Georges et al. | |
| 2015/0202051 A1* | 7/2015 | Tanaka | A61F 2/4657 623/17.16 |
| 2016/0220388 A1* | 8/2016 | Flores | A61F 2/4611 |
| 2017/0312096 A1* | 11/2017 | Liu | A61F 2/4455 |
| 2017/0340358 A1* | 11/2017 | Bullard | A61B 17/1757 |
| 2018/0049756 A1* | 2/2018 | Livorsi | A61B 17/8894 |

\* cited by examiner

SPINAL FIXATION AND GUIDANCE SYSTEM AND METHOD

TECHNICAL FIELD

The invention relates to a spinal fixation and guidance system and a method of use. In particular, the invention relates, but is not limited, to a spinal fixation and guidance system and method that may be suitable for use in vertebrae fusion.

BACKGROUND

The discussion of any prior art documents, techniques, methods or apparatus is not to be taken to constitute any admission or evidence that such prior art forms, or ever formed, part of the common general knowledge.

Spinal fusion surgery is intended to prevent the movement of painful vertebrae. In particular, spinal fusion surgery limits motion between adjacent vertebrae by creating a fusion environment therebetween.

A common method of stabilising and limiting the motion between adjacent vertebrae is, after the insertion of an intervertebral cage, securing screws through and via the intervertebral cage into the adjacent vertebral bodies. Securing the intervertebral cage with screws to the vertebrae normally involves screwing fasteners, through apertures in the cage and into prepared holes in the vertebrae.

A problem associated with implantation of the cage and insertion of integral screws through the cage into bone is limited visualization through a small 30 incision and utilising and or securing an adequate alignment guide for the correct screw trajectory during both preparation of screw holes and initial screw insertion. Migration of the cage and incorrect trajectory or angle, either during hole preparation or screw fastening, can jeopardise precise placement of both the cage and screw. This may lead to further complications including, for example, the cage migrating posteriorly during screw insertion and coming into contact with posterior neural and vascular structures; the preparation of the screw hole at the incorrect angle or trajectory therefore not gaining adequate bone purchase; or the inadequate fixation of the cage to the vertebrae and therefore affecting construct stability and increased risk of pseudoarthrosis.

Further, there is an additional known risk associated with integral screw fixation through a spinal cage directly fastened into bone not providing required or adequate stability or rigidity due to inadequate bone or unexpected spinal instability. This lends to the requirement of a completely separate plate and screw system to be applied to the vertebral segment and therefore a wider surgical incision to be made. A plate, cage and screw system is often required to be on standby should an intraoperative change of surgical procedure be necessary.

Accordingly, there is a need for providing a spinal fixation and guidance system and a method of use that addresses some of the problems associated with the prior art.

SUMMARY OF THE INVENTION

In a first aspect, the invention provides a spinal fixation and guidance system comprising:
    a spinal cage configured to be received between adjacent first and second vertebrae; and
    an alignment assembly comprising:
        a mating element comprising a first engagement portion for engagement with the spinal cage and a second engagement portion for engagement with a guiding assembly, the mating element being adapted to be releasably connected to the spinal cage;
        wherein the guidance assembly further comprises: a guidance element comprising guiding portions for guiding one or more fasteners for fastening said spinal cage relative to said adjacent vertebrae In an embodiment, the guidance element is of a first type or a second type wherein the guidance element of the first type guides fasteners for fastening the implant directly to bone tissue surrounding said implant and wherein the guidance element of the second type guides and aligns a spinal plate by fastening the guidance element of the second type to the mating element adjacent to the said vertebrae; and wherein in a first operable configuration the engagement portion of the mating element is configured to engage the guidance element of the first type and in a second operable configuration the mating element is adapted to engage the guidance element of the second type.

Preferably, the guidance element of the first type comprises one or more guiding passages for guiding said fasteners into corresponding one or more fastener receiving apertures provided along an in-use side wall of the implant at a pre-determined angle for fastening said implant to bone tissue; and/or the guidance element of the second type comprises a plate positioning and holding portion for engagement to the spinal plate, and said plate further comprising: at least a first aperture to fasten the spinal plate to the first vertebrae; and at least a second aperture to fasten the spinal plate to the second vertebrae In an embodiment, the guiding element is configured to move along a length of the mating element.

In an embodiment, the guiding assembly further comprises:
    an in-use upper body and in-use lower body whereby:
        the in-use upper body comprises a drive-engagement portion for receiving a drive unit for driving said guide element along a of the mating element; and
        the in-use lower body comprises an implant engagement portion for engaging the spinal cage or spinal plate during use.

In an embodiment, the mating element comprises a releasable connector for releasably connecting the mating element to the spinal cage.

Preferably, the releasable connector comprises a shaft extending between a driver attachment portion and a head portion wherein the driver attachment portion is adapted to be coupled to a driver and the head portioned is adapted to be coupled to the mating element.

In an embodiment, the mating element comprises an elongate body extending between two ends wherein the engagement portions are positioned along an outer wall of the elongate body for engaging said guide element and preferably allowing the guide element to move along a length of the elongate body during use.

In an embodiment, the engagement portion comprises helical threads for engaging complementary threads provided along a receiving portion of the guide element to allow the guide element to be moved along a length of the elongate body of the mating element.

In an embodiment, the guiding element (option 2) further comprises a holding and alignment member for preventing relative movement between the mating element and the spinal plate.

Preferably, the upper engagement portion of the guidance element (option 2) comprises helical threads positioned along an inner wall to engage with the threaded elongate body of the mating element.

In an embodiment, the mating element comprises a first engagement portion for engagement with the guidance element and a second threaded portion for engagement with a receiving portion of the implant.

In an embodiment the spinal fixation and guidance system further comprises a securing arrangement for releasably securing said mating element to the implant.

In another aspect, the invention provides a mating apparatus for mating a guidance assembly relative to a spinal cage received between adjacent first and second vertebrae, the mating apparatus comprising:
  engagement portions for mating with said guidance assembly to position the guidance assembly in a fastening position to allow fasteners to be guided by the guiding element for fastening the spinal cage relative to said adjacent vertebrae
  wherein in a first operable configuration the engagement portion of the mating element engages the guidance assembly of a first type and in a second operable configuration the mating element engages the guidance element of a second type.

In yet another aspect, the invention provides a method for spinal fixation, the method comprising the steps of:
  positioning a spinal cage in between adjacent first and second vertebrae;
  releasably connecting a mating element to said spinal cage; and
  engaging a guidance element relative to the mating element and moving the guidance element along a length of the mating element to position said guidance element in a fastening position whereby in the fastening position one or more guidance apertures in the guidance element are substantially in alignment with respective one or more fastener receiving apertures provided in the in-use side walls of the spinal cage;
  fastening said spinal cage relative to the first and second vertebrae by guiding said fasteners through one or more guiding apertures and fastener receiving apertures; or
  positioning a spinal plate relative to the releasably connected mating element and moving a guidance element along a length of the mating element to position, align and hold a spinal plate relative to the spinal cage;
  fastening said spinal plate relative to the first and second vertebrae by inserting fasteners through one or more apertures.

BRIEF DESCRIPTION OF THE DRAWINGS

The Detailed Description is not to be regarded as limiting the scope of the preceding Summary of the Invention in any way. The Detailed Description will make reference to a number of drawings as follows.

DETAILED DESCRIPTION OF PREFERRED EMBODIMENT

FIG. 1 illustrates a mating element 10 in a coupled configuration with a driver 200. The mating element 10 comprises a head portion 13 that is configured to be coupled with a receiving portion 22 of the spinal fusion cage (shown in FIGS. 1B and 1C).). Each mating element 10 comprises an elongate body that extends between drive attachment portion 17 and the head portion 12 having a first threaded portion 14 that extends along the substantial length of the elongate body is positioned along the elongate body of the mating element 10 and a second threaded portion 16 that is located at a frontal or proximal end of the mating element 10.

Figure 1A:
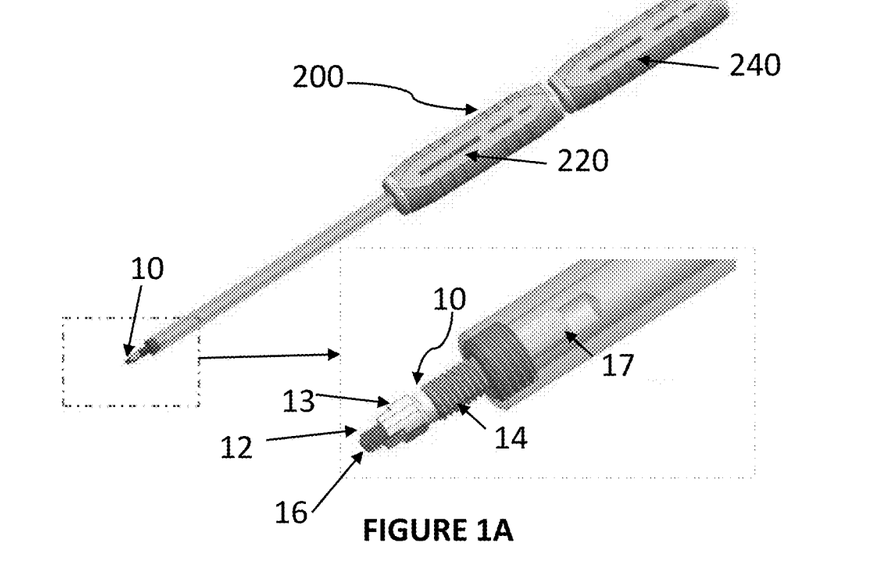
FIG. 1A is a perspective view of a mating element 10 coupled with a driver 200 in accordance with an embodiment.
Figure 1B:
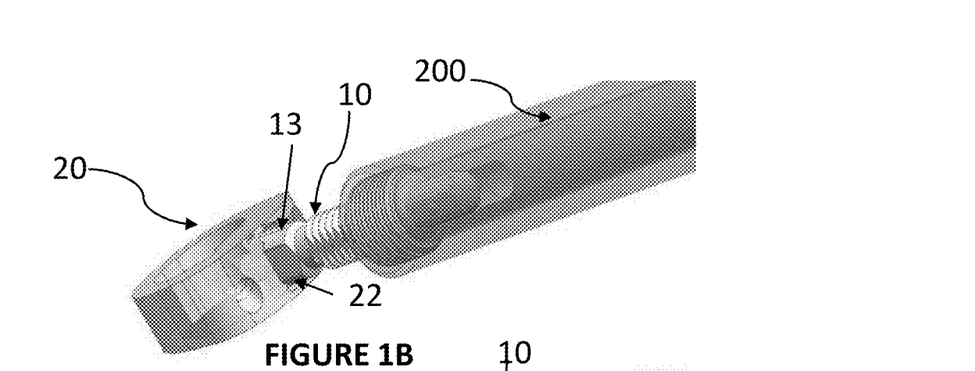
FIG. 1B illustrates a spinal fusion cage 20 coupled with the mating element 10. The mating element 10 is in a coupled configuration with the driver 200.
Figure 1C:
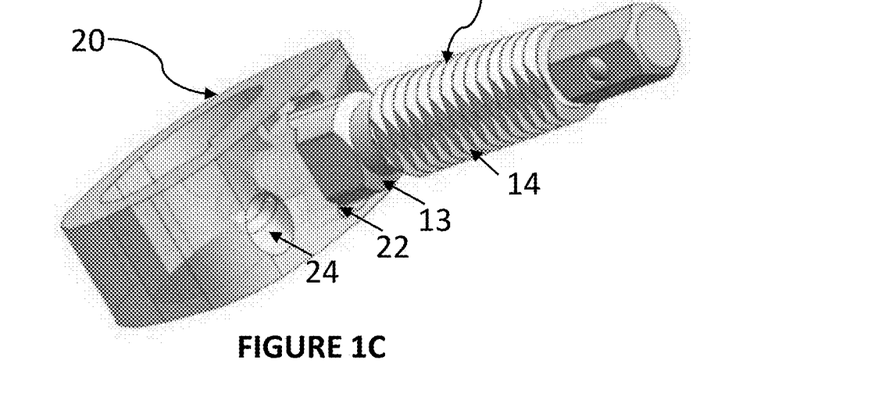
FIG. 1C illustrates the spinal fusion cage 20 coupled with the mating element 10. The mating element 10 is in an uncoupled configuration relative to the driver 200.
Figure 1D:
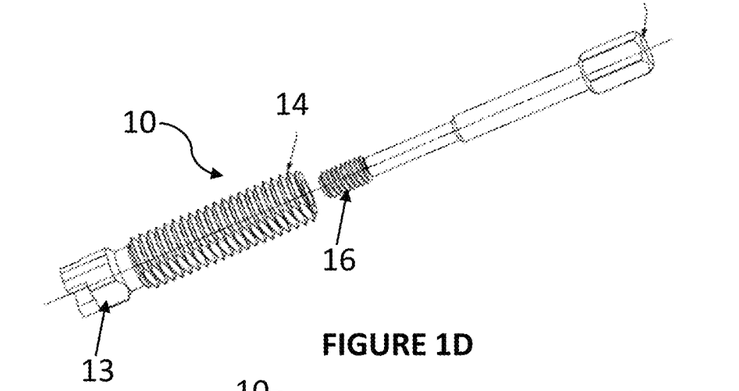
FIG. 1D is an exploded view of the mating element 10.
Figure 1E:
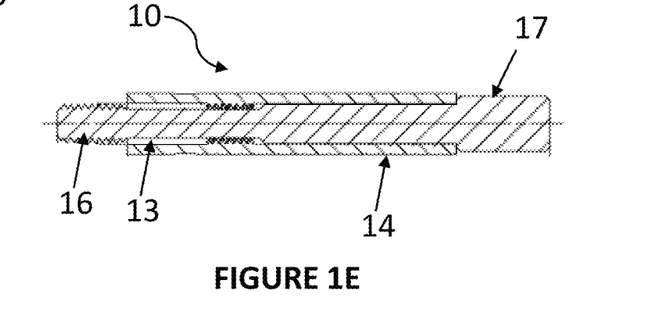
FIG. 1E is a sectional view of the mating element 10.
Figure 1F:
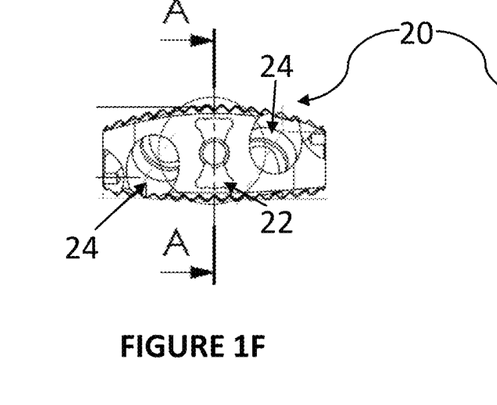
FIG. 1F is a frontal view of the spinal fusion cage 20.
Figure 1G:
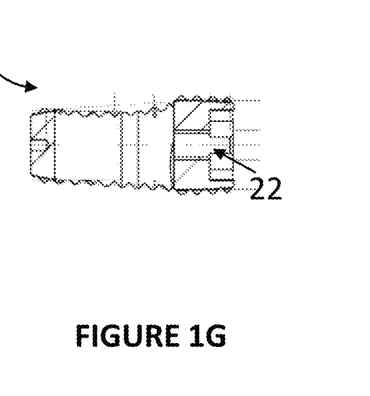
FIG. 1G is a sectional view of the spinal fusion cage 20.

The configuration of the mating element 10 allows each of the threaded portions 14 and 16 to be driven independently of each other. As a result, the forwardly located threaded portion 16 may be used for coupling the head portion 13 of the mating element with the receiving portion 22 of spinal fusion cage 20. In a spinal fixation method involving the use of the system 100, the driver 200 may be used for coupling the mating element 10 with the spinal cage 20. In the preferred embodiment, the driver 200 comprises two drive shafts driven by rotatable handles 220 and 240 that can be rotated independently of each other. As a result, the forwardly located threaded portion 16 may be threadably engaged with the receiving portion 22 of the cage by rotating one of the handle 240. Once the mating element 10 is engaged and secured with spinal cage 20 (as shown in FIG. 1B), the other of the handles 220 may be rotated to uncouple the first threaded portion 14 from the coupling end 60 of the driver 200 (shown in FIG. 1C). Advantageously, the locking body 13 located adjacent to the frontal threaded portion 16 may also be used for securing the mating element 10 to the spinal fusion cage 20.

Figure 2A:
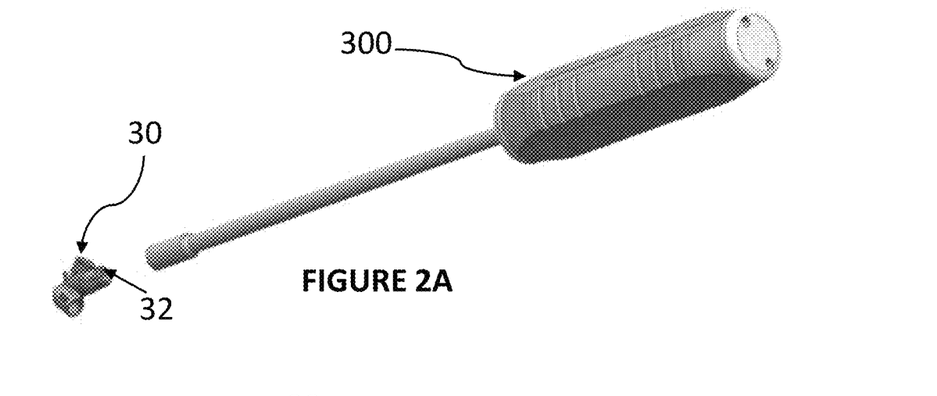
FIG. 2A illustrates a guiding element 30 (first type) in an uncoupled configuration relative to a driver 300 in accordance with an embodiment.
Figure 2B:
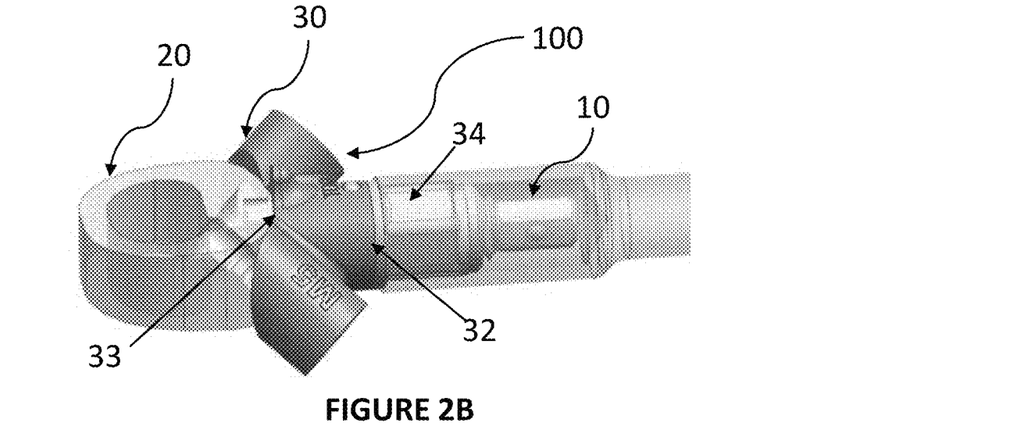
FIG. 2B illustrates the guiding element 30 (first type) coupled with the spinal cage 20 at one end and coupled with the driver 300 at another end.
Figure 2C:
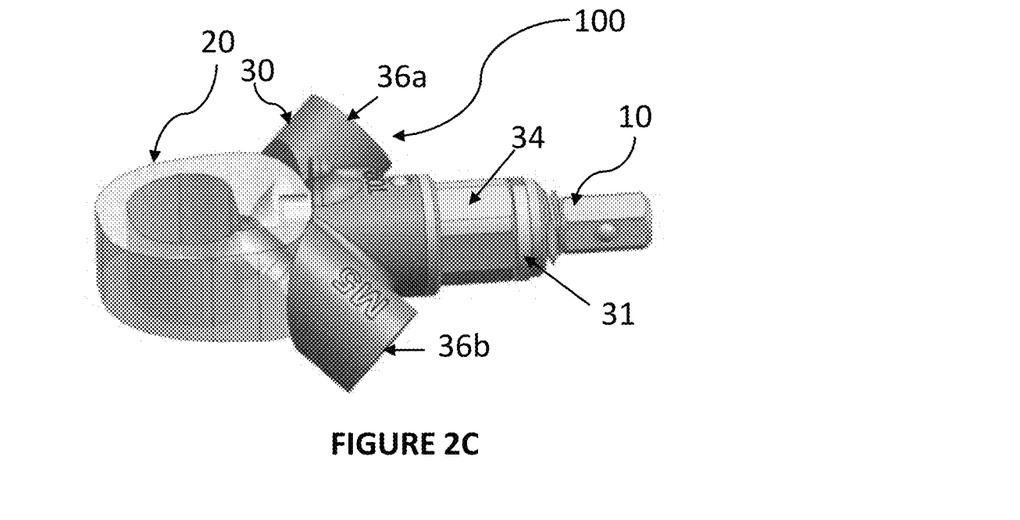
FIG. 2C illustrates the guiding element 30 (first type) coupled with the spinal cage 20 at one end with the driver 300 being uncoupled relative to the other end.
Figure 2D:
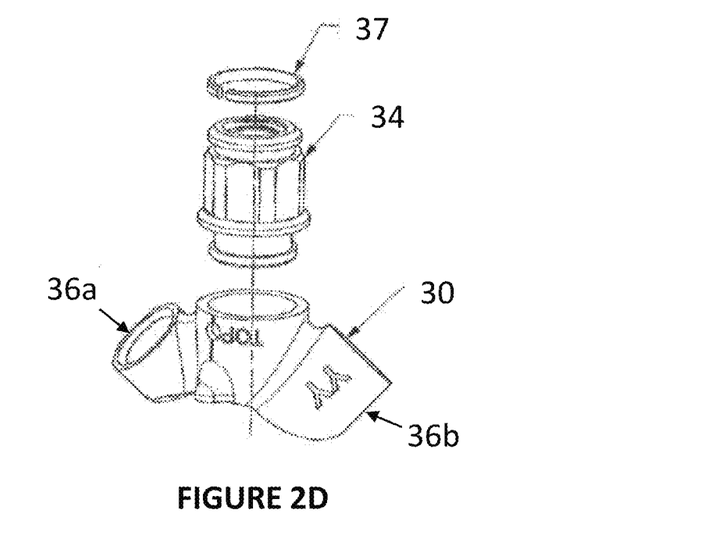
FIG. 2D is an exploded view of the first guiding arrangement/assembly incorporating the guiding element 30.
Figure 2E:
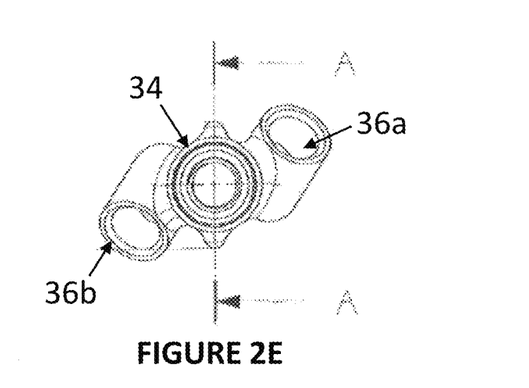
FIG. 2E is a top view of the first guiding arrangement/assembly incorporating the guiding element 30.
Figure 2F:
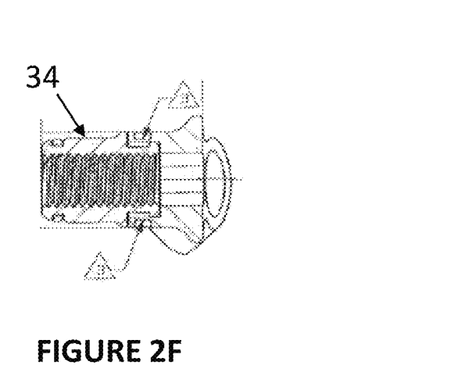
FIG. 2F is a sectional view (along A-A) of the first guiding arrangement/assembly incorporating the guiding element 30.
Figure 2G:
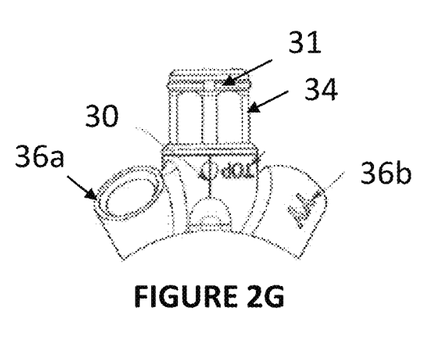
FIG. 2G is a first perspective view of the first guiding arrangement/assembly in an assembled configuration.
Figure 2H:
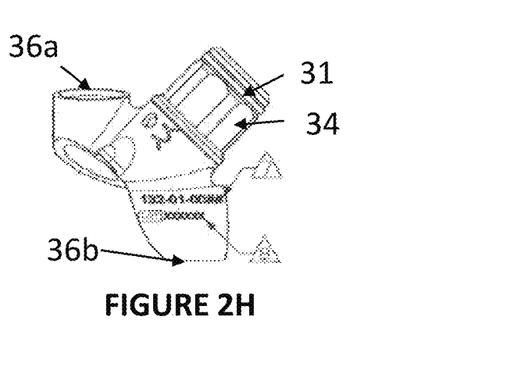
FIG. 2H is a second perspective view of the first guiding arrangement/assembly in an assembled configuration.
Figure 3A:
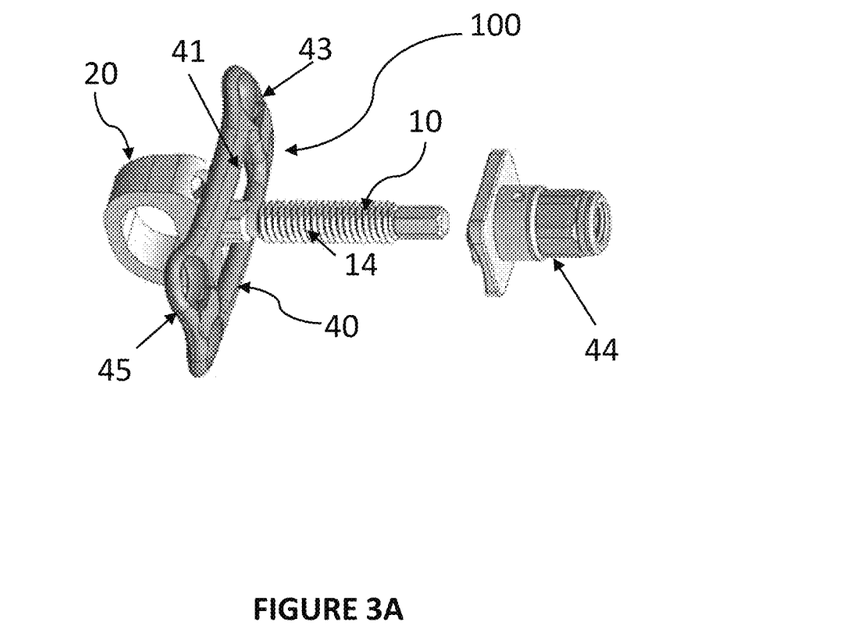
FIG. 3A illustrates a first view of the guiding element 48 (second type) in an uncoupled configuration relative to the spinal plate 40 and spinal cage 20 in accordance with an embodiment.
Figure 3B:
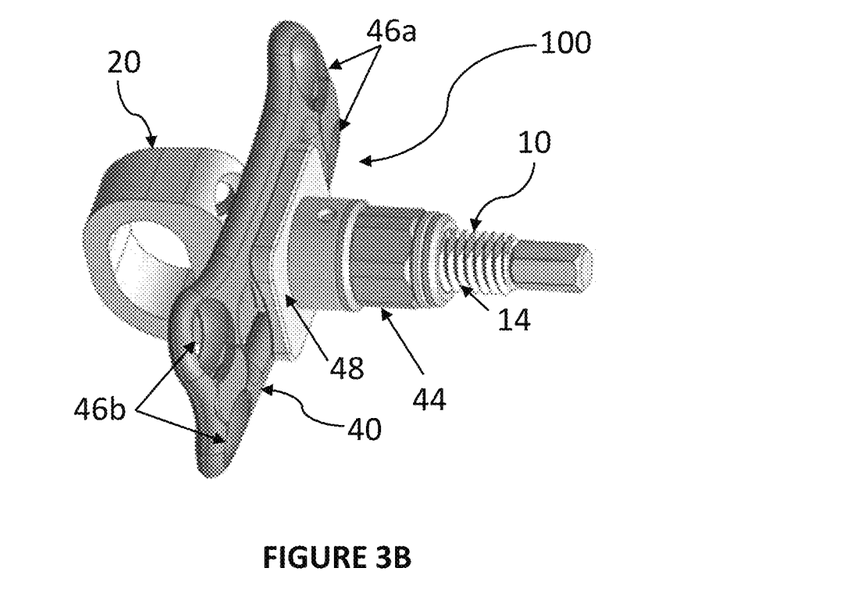
FIG. 3B illustrates a second view of the guiding element 48 (second type) in a coupled configuration relative to the spinal plate 40 and spinal cage 20.
Figure 3C:
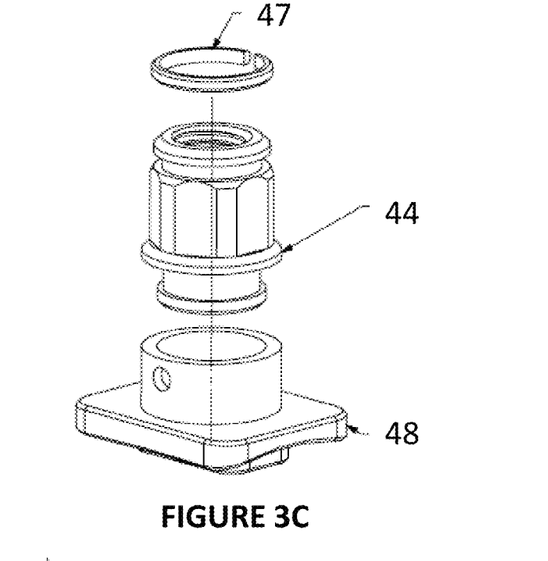
FIG. 3C is an exploded view of the guidance arrangement/assembly (second type) for the guiding element 48.
Figure 3D:
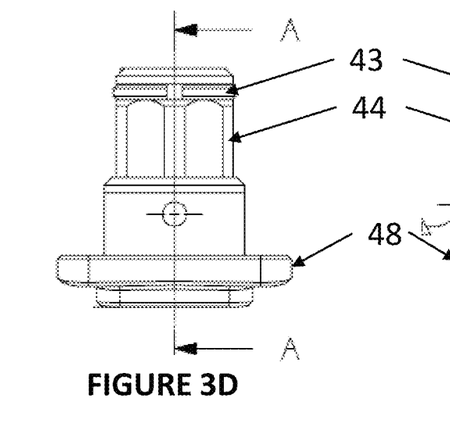
FIG. 3D is a side view of the guidance arrangement/assembly (second type) for the guiding element 48.
Figure 3E:
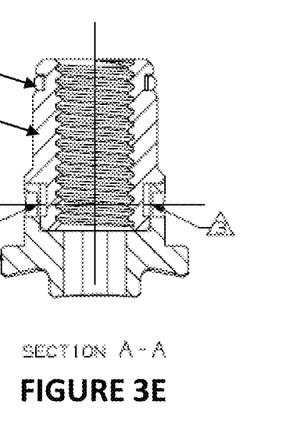
FIG. 3E is a sectional view (along A-A) for the guiding arrangement/assembly (second type).
Figure 3F:
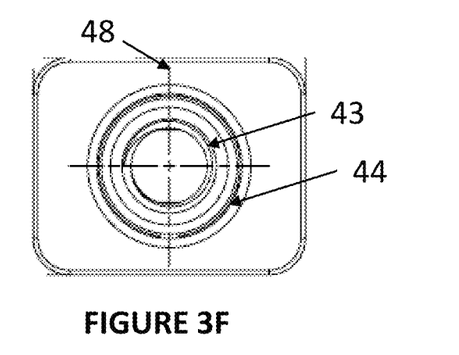
FIG. 3F is a top view of the guiding arrangement/assembly (second type) for the guiding element 48.
Figure 4A:
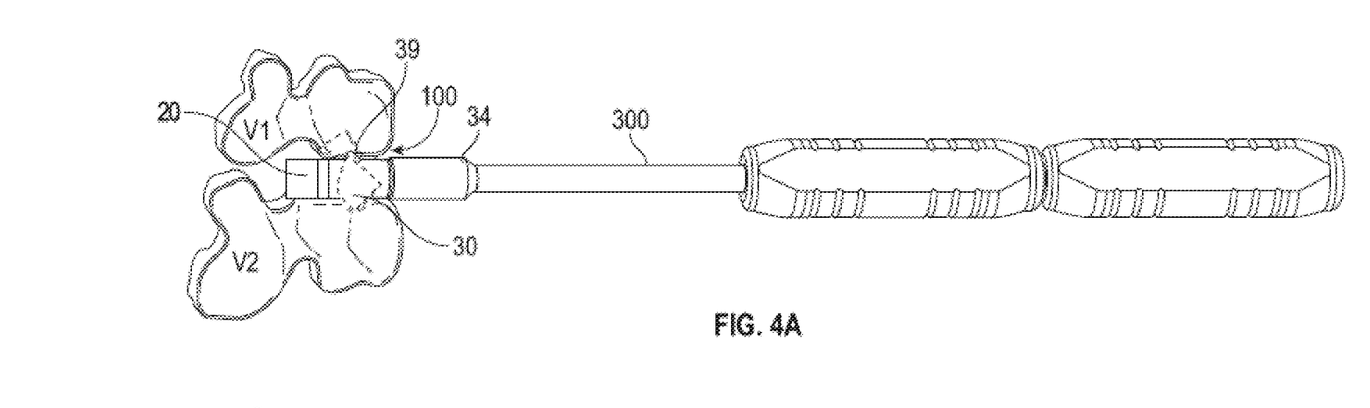
FIG. 4A illustrates an in-use sectional view of the spinal fixation and guiding system 100 utilising the guiding element 30 (first type) for spinal fusion of adjacently located vertebrae V1 and V2.
Figure 4B:
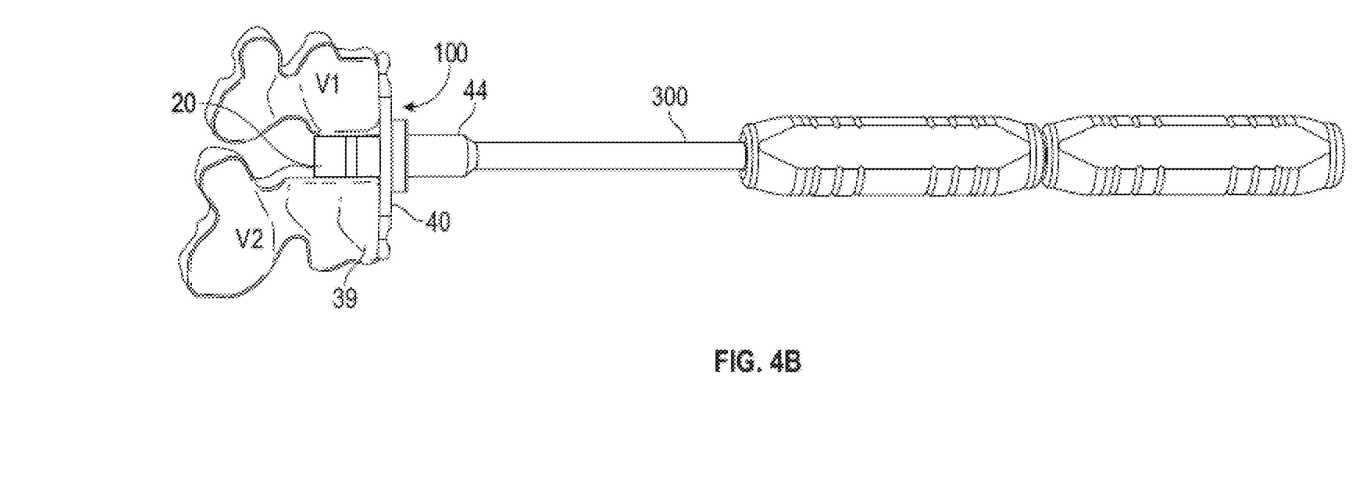
FIG. 4B illustrates an in-use sectional view of the spinal fixation and guiding system 100 utilising the guiding element 48 (second type) for spinal fusion of adjacently located vertebrae V1 and V2.

Referring to FIGS. 2 to 4, a spinal guiding and fixation system 100 in accordance with an embodiment of the present invention is illustrated. The system 100 is provided for guiding and fixing a spinal implant, specifically a spinal fusion cage 20 in between adjacently located vertebrae (V1 and V2—shown in FIGS. 4A and 4B). The spinal guiding and fixation system 100 provides an improvement over prior art systems for guiding fasteners to allow fixing of the spinal fusion cage 20 in between adjacent vertebrae (V1 and V2) during spinal fusion surgery.

Once the driver 200 is uncoupled from the mating element 10, the next step involves positioning a guiding element 30 of a first type (shown in FIGS. 2A to 2C) along the threaded portion 14 of the mating element 10 (in engagement with the spinal fusion cage 20). Driver 300 is coupled with an upper drive-engagement portion 34 of the guiding element 30 to move the guide element along the threaded portion 14 of the mating element 10. The upper drive engagement portion 34 comprises a threaded opening comprising helical threads for engagement with the threaded portion 14 of the mating element 10. The positioning arrangement for the guiding element 30 comprises the upper drive engagement member 34 having a threaded opening for engagement with the threaded portion 14 of the mating element 10. The forward end of the guiding element 30 also comprises an implant engagement portion 33 that engages with the receiving portion 22 of the implant 20 once the guiding element 30 has moved along the length of the treaded portion 14. During use, the driver 300 drives the guiding element 30 along the threaded portion 14 until the implant engagement portion 33 is engaged and secured to the receiving portion 22 of the spinal fusion cage 20. The stop member 34 functions as a locking screw and an initial step involves inserting an O-ring 37 into the groove provided along an upper portion of the drive engagement member 34. The member 34 is then placed into a central opening (positioned between the guiding passages 36a and 36b) and a thin section of the wall defining the opening is punched to hold the stop member in position within the opening. As discussed, the drive engagement member 34 includes helical threads to allow the guiding element 30 and the drive engagement member 34 to be moved along the threaded portion 14.

The forward end of the guiding element assembly also comprises an implant engagement portion 33 that engages with the receiving portion 22 of the implant 20. The driver 300 drives the guiding element 30 along the threaded portion 14 until the implant engagement portion 33 is engaged and secured to the receiving portion 22 of the spinal fusion cage 20.

In the preferred embodiment, the engagement portion 34 may be used for positioning the guiding element 30 in an operable configuration. The engagement portion 34 comprises a threaded opening and allows the engagement portion 34 to be engaged along the length of the threaded portion 14 of the mating element 10 before the guiding element 30 is secured to the cage implant 20. During use, a driver (such as driver 300) can be used for moving the guiding element 30 along the threaded portion 14 along the length of the mating element 10.

The guiding element 30 also comprises guiding passages 36a and 36b for guiding fasteners in the form of screws 39 into corresponding fastener receiving apertures 24 provided along an in-use side wall of the spinal fusion cage 20 at a pre-determined angle (provided by the guiding passages 36a and 36b) for fastening said cage 20 to bone tissue of adjacently located vertebrae V1 and V2 as shown in FIG. 4A. The guiding element 30 enables precision and reproducible placement of the fasteners along a pre-determined trajectory resulting in the cage 20 being engaged with bone tissue in a desirable and consistent manner, as intended every time. Without the use of the guiding element 30, it often very difficult in a minimal incision with limited visualisation for a surgeon to gauge the exact angle of inclination at which the screws or fasteners should be inserted into the fastener receiving apertures of the cage 20. Insertion of the screws or fasteners 39 at an incorrect angle can result in skiving of the screw on vertebral endplates with no engagement of adjacent bone. This often leads to removal and or revision of spinal fusion cage and screw placement. Alternatively, in the absence of the guiding element 30, the screws or the fasteners can be over-angulated leading to posterior perforation of the screw into the spinal canal. Once the cage 20 has been fastened and secured the guiding element 30 and mating element 10 may be uncoupled from the cage 20 as a single one step assembly by utilising 200 and 240 simultaneously. Subsequently, the mating element 10 may be removed separately using driver such as 300 after the guidance element is uncoupled from the cage 20 by using a driver such as 240.

In some instances, the use of fasteners to fasten the spinal cage 20 directly to bone tissue may not be suitable particularly when the patient's bone is discovered to be soft, osteoporotic or particularly when there is instability in the vertebrae. In such instances, the guiding element of the first type 30 is replaced by a guiding element of a second type 48 and a spinal plate 40 with subsequent fasteners as shown in FIGS. 3A and 3B. The guiding element 48 of the second type comprises an upper drive engagement portion 44 with a threaded opening comprising helical threads for engagement with the threaded portion 14 of the mating element 10. The forward end of the guiding assembly comprises a holding and alignment portion 48 that engages, holds and aligns the spinal plate 40 relative to the spinal cage 20. The upper drive engagement portion 44 receives the threaded portion 14 of the mating element 10. Again the initial step involves inserting a retaining O-ring 47 into the groove located along the drive engagement member 44. A male connecting portion of the drive engagement member 44 is positioned into an opening of a spacer member 48 and a thin section of the wall defining the opening is punched to hold the stop member 44 in position.

The spinal plate 40 includes two or more holes 46a and 46b that are located in a spaced apart configuration. The step of positioning the spinal plate 40 on the mating element 10 involves aligning spinal plate 40 relative to the mating element 10. Using a driver (such as a driver 300) the guiding element 48 moves along the threaded portion 14 of the mating element 10. In the preferred embodiment, the guiding element 48 may be used for positioning, aligning and holding the spinal plate 40 in an operable configuration. The guidance element 48 comprises an engagement portion identical to guiding element option 1 which has a threaded opening and allows the forward portion of the guiding element 48 to be engaged along the length of the threaded portion 14 of the mating element 10 before the guiding element 48 is secured to the spinal plate 40. The spinal plate 40 is positioned relative to and in between the guiding element 8 and the spinal cage 20. Preferably, the guiding element 48 is attached to one end of the upper engagement portion 44. Upon moving the engagement portion 44 along the length of the mating element 10, the forward end of the guiding element 48 pushes the spinal plate 40 into a desirable and optimal fastening position. During use, a driver (such as driver 300) can be used for moving the guiding element 48 along the length of the mating element 10 and positioning the spinal plate 40 into a fastened or secured configuration relative to the cage implant 20 and to align the plate holes 46a and 46b to the adjacent vertebrae V1 and V2 as shown in FIG. 4B.

The guide plate 40 included an elongate slot 41 that is positioned in between end portions 43 and 45. Each of the end portions 43 and 45 include pairs of screw receiving apertures or plate holes 46a and 46b that allow each of the 2s end portions 43 and 45 to be fastened and secured to vertebrae V1 and V2 respectively. The elongate slot 41 is sufficiently sized for receiving the elongate body of the mating element 10 in a transverse configuration. The elongate shape of the slot 41 allows the position of the guide plate 40 to be adjusted. By way of example, during spinal fusion surgery, the guide plate 40 may need to be moved in a slightly upwardly or downwardly direction to ensure placement of the guide plate in a precise manner.

The forward portion of the guiding element 48 is useful in temporarily fixing the spinal plate 40 relative to the adjacent vertebrae V1 and V2 whilst simultaneously aligning the spinal plate 40 relative to the position of the cage implant 20. Such an arrangement allows the spinal plate 40 to be positioned in a precise manner relative to the disc space thereby allowing for precision screw placement for securing the spinal plate 40 to the adjacent vertebrae by inserting screws or fasteners into the plate holes 46a and 46b. It is often a problem if the spinal plate 40 is positioned too close to either end of the adjacent vertebral bodies. Precision plate placement is required relative to the disc space (even on both sides) to ensure any adjacent disc space is not impinged upon by the plate placement. The insertion of the fasteners or screws through the pairs of plate holes 46a and 46b to fasten the spinal plate 40 to the adjacently located vertebrae with the cage body positioned there-between secures the spinal cage 20 in position relative to the adjacently located vertebrae (not shown).

It is also important to note that the mating element 10 in the presently described embodiment comprises a suitable configuration that allows the guide element of the first type (30) or the guide element of the second type (48) to be used for spinal fusion involving the spinal cage 20. Specifically, the elongate body portion comprising the first threaded portion 14 is suitable for engagement with the guide element of the first type (30—that allows the cage implant 20 to be directly fastened to the bone tissue using screws—FIG. 4A) or the guide element of the second type (guide plate 48 secured to the cage implant 20 and fastened to the adjacent vertebrae V1 and V2 as shown in FIG. 4A). The configuration of the mating element 10 allows the use of the same drivers and mating element for either guiding elements 30 or 48. The use of either type of guiding elements 30 or 48 in conjunction with the mating element 10 allows common instrumentation (such as drivers and mating elements 10) to be used. The surgical space in which the spinal fusion surgery occurs in is often a minimal invasive (small) incision. As a result, the guidance and fixation system must be low profile and intuitive as access and visualisation is often extremely limited. The use of the system 100 allows for precision placement and flexibility of either guiding element 30 or 48 (first type or second type) with limited visual and tactical feedback. If the patient requirements change intraoperatively from (the first type to the second type) there is no need to change implants 20, mating elements 10 or drivers 200 or 300. As a result, the spinal fixation and guidance system 100 described herein addresses some of the shortcomings of the prior art and allows the surgeon to easily switch between the use of guiding element 30 or 48 depending on the specific requirements and circumstances of the patient without significantly increasing the duration or complication during surgery.

In compliance with the statute, the invention has been described in language more or less specific to structural or methodical features. The term "comprises" and its variations, such as "comprising" and "comprised of" is used throughout in an inclusive sense and not to the exclusion of any additional features.

It is to be understood that the invention is not limited to specific features shown or described since the means herein described comprises preferred forms of putting the invention into effect.

The invention is, therefore, claimed in any of its forms or modifications within the proper scope of the appended claims appropriately interpreted by those skilled in the art.

What is claimed is:

1. A spinal fixation and guidance system comprising:
    a spinal cage configured to be received between adjacent first and second vertebrae; and
    an alignment assembly comprising:
        a mating connector including an elongate body having two ends, a first engagement portion adjacent a first end for engagement with the spinal cage and a second engagement portion intermediate the first and second ends for engagement with a guidance assembly, the mating connector being adapted to be releasably connected to the spinal cage;
    wherein the guidance assembly further includes a guide comprising guiding portions for guiding one or more fasteners for fastening said spinal cage relative to said adjacent vertebrae; and
    wherein the second engagement portion comprises threads for engaging with complementary threads provided along a receiving portion of a positioner and is positioned along an outer surface of the elongate body to allow the guide to be moved along a length of the elongate body of the mating connector;
    wherein the guide is of a first type or a second type wherein the guide of the first type guides fasteners for fastening the spinal cage directly to bone tissue surrounding said implant and wherein the guide of the second type allows temporary fastening of a spinal plate to the mating connector to allow the spinal plate to be fastened simultaneously to the implant and the adjacent vertebrae; and wherein in a first operable configuration the engagement portion of the mating connector is configured to engage the guide of the first type and in a second operable configuration the mating connector is adapted to engage the guide of the second type.

2. A spinal fixation and guidance system in accordance with claim 1 wherein:
the guide of the first type comprises one or more guiding passages for guiding said fasteners into corresponding one or more fastener receiving apertures provided along an in-use side wall of the implant at a pre-determined angle for fastening said implant to bone tissue; and/or
the guide of the second type comprises a plate positioning and holding portion for engagement to the spinal plate, and said plate further comprising: at least a first aperture to fasten the spinal plate to the first vertebrae; and at least a second aperture to fasten the spinal plate to the second vertebrae.

3. A spinal fixation and guidance system in accordance with claim 1, wherein the guidance assembly further comprises:
an in-use upper body and in-use lower body whereby:
the in-use upper body comprises a drive-engagement portion for receiving a driver for driving said guide element along a length of the mating element; and
the in-use lower body comprises an implant engagement portion for engaging the spinal cage or spinal plate during use.

4. A spinal fixation and guidance system in accordance with claim 1, wherein the mating connector comprises a releasable connector for releasably connecting the mating connector to the spinal cage.

5. A spinal fixation and guidance system in accordance with claim 4 wherein the releasable connector comprises a shaft extending between a driver attachment portion and a head portion adapted to be coupled to the implant during use.

6. A spinal fixation and guidance system in accordance with claim 1, wherein the threaded second engagement portion comprises helical threads provided along an outer wall of the elongate body.

7. A spinal fixation and guidance system in accordance with claim 1, wherein the positioner further comprises a holding and positioning portion for preventing relative movement between the mating element and the guide element.

8. A spinal fixation and guidance system in accordance with claim 7 wherein the holding and positioning portion comprises helical threads positioned along an inner wall of the receiving portion to engage with the threaded elongate body of the mating connector.

9. A spinal fixation and guidance system in accordance with claim 1, wherein the mating connector comprises a first threaded engagement portion for engagement with a receiving portion of the spinal cage.

10. A spinal fixation and guidance system in accordance with claim 1, further comprising a releasable fastener for releasably securing said mating connector to the spinal cage.

11. A mating apparatus in combination with a guidance assembly for mating the guidance assembly relative to a spinal cage received between adjacent first and second vertebrae, the mating apparatus comprising:
a mating connector including an elongate body extending between two ends having at least one engagement portion positioned along an outer surface of the elongate body for mating with said guidance assembly to position the guidance assembly along a length of the elongate body to guide one or more fasteners for fastening said spinal cage relative to said adjacent vertebrae;
wherein in a first operable configuration the engagement portion of the mating connector engages the guidance assembly of a first type and in a second operable configuration the mating element engages the guidance assembly of a second type;
wherein the guidance assembly of the first type guides fasteners for fastening the implant directly to bone tissue surrounding said spinal cage and wherein a guide of the guidance assembly of the second type guides fasteners to fasten the guide of the second type to the spinal cage and the adjacent vertebrae; and wherein in a first operable configuration the engagement portion of the mating connector is configured to engage a guide of the guidance assembly of the first type and in a second operable configuration the mating connector is adapted to engage the guide of the second type.

12. A mating apparatus in accordance with claim 11, wherein the mating apparatus comprises a releasable connector for releasable connection to the spinal cage such that upon fastening the implant relative to the adjacent vertebrae, the mating apparatus can be uncoupled from the spinal cage.

13. A mating apparatus in accordance with claim 12 wherein the releasable connector comprises a shaft extending between a driver attachment portion and a head portion, the head portion being adapted to be releasably coupled to the spinal cage during use.

14. A mating apparatus in accordance with claim 13 wherein the elongate body of the mating connector extends between the releasable connector and the head portion; and
wherein a first engagement portion is positioned adjacent said head portion and a second engagement portion is positioned along an outer wall of the elongate body for engaging said guide during use.

15. A mating apparatus in accordance with claim 14 wherein the second engagement portion comprises threads for engaging complementary threads provided along a receiving portion of the guidance assembly to allow the guide to be moved along said length of the elongate body of the mating connector.

16. A method for spinal fixation, the method comprising the steps of:
positioning a spinal cage in between adjacent first and second vertebrae;
releasably connecting a mating connector to said spinal cage, the mating connector including an elongate body having two ends with a first engagement portion adjacent one end for engagement with the spinal cage and a second engagement portion comprising threads for engaging with complementary threads provided along a receiving portion of a positioning arrangement;
selecting a guide of either a first type or a second type wherein the guide of the first type guides fasteners for fastening the spinal cage directly to bone tissue surrounding said implant and wherein the guide of the second type allows temporary fastening of a spinal plate to the mating connector to allow the spinal plate to be fastened simultaneously to the implant and the adjacent vertebrae;
engaging the selected guide with the second engagement portion positioned along an outer surface intermediate the first and second ends of the elongate body of the mating connector;
moving the guide along a length of the mating connector to position said guide in a fastening position whereby in the fastening position one or more guiding passages in the guide are substantially in alignment with respective one or more fastener receiving apertures provided in side walls of the spinal cage; and fastening said spinal cage relative to the first and second vertebrae by guiding fasteners through one or more guiding passages and fastener receiving apertures.

17. A spinal fixation method in accordance with claim 16 including the further step of disengaging the guide from the spinal cage subsequent to fastening said spinal cage to each vertebrae.

\* \* \* \* \*